United States Patent
Hamburger et al.

[11] Patent Number: 5,995,686
[45] Date of Patent: Nov. 30, 1999

[54] FIBER-OPTIC SENSOR DEVICE AND METHOD

[76] Inventors: Robert N. Hamburger, 9485 La Jolla Shores Dr., La Jolla, Calif. 92037-1149; Ruibo Wang, 6657 El Colegio Rd., Apt. 9, Goleta, Calif. 93117; Jien-Ping Jiang, 2350 E. Water St., Apt. B211, Tuscon, Ariz. 85719

[21] Appl. No.: 08/991,086

[22] Filed: Dec. 16, 1997

[51] Int. Cl.$^6$ ........................................ G02B 6/10
[52] U.S. Cl. ............................. 385/12; 385/128
[58] Field of Search ................ 250/227.11, 227.14; 356/133; 385/12, 147, 123, 128

[56] References Cited

U.S. PATENT DOCUMENTS

| | | | |
|---|---|---|---|
| 4,575,181 | 3/1986 | Ishikawa | 350/96.2 |
| 4,851,817 | 7/1989 | Brossia et al. | 340/583 |
| 4,994,682 | 2/1991 | Woodside | 250/577 |
| 5,005,005 | 4/1991 | Brossia et al. | 340/604 |
| 5,695,583 | 12/1997 | Van Den Bergh et al. | 156/153 |

*Primary Examiner*—Hung N. Ngo
*Attorney, Agent, or Firm*—Brown, Martin, Haller & McClain, LLP

[57] ABSTRACT

A sensor system includes an optical fiber sensor element which is connected to a light source at one end and a detector at the opposite end. The sensor element is an optical fiber which has a light transmitting core, a cladding layer surrounding the core, and an outer protective layer. The outer protective layer is removed along at least part of the length of the fiber to expose a portion of the cladding layer, and the exposed portion of the cladding layer is roughened to produce a plurality of surface scratches extending through at least part of the thickness of the cladding layer. The exposed, roughened portion of the cladding layer forms a sensor region through which light is lost from the core, and is exposed to a medium to be monitored so that the amount of light lost will be dependent on the refractive index of the medium.

14 Claims, 1 Drawing Sheet

FIBER-OPTIC SENSOR DEVICE AND METHOD

BACKGROUND OF THE INVENTION

The present invention relates generally to sensor devices and methods for monitoring conditions in a surrounding medium, and is particularly concerned with fiber-optic sensor devices.

It is often important to be able to monitor various properties in gaseous and liquid media. Some properties which can be critical are humidity, contaminant levels, pollutant levels, battery solution composition, and so on.

Current means of measuring air humidity involve either a special polymer sensor head whose capacitance is dependent on the amount of moisture it absorbs, or a dew point meter. Both have adequate accuracy, bit are slow in response time and expensive to manufacture.

Some proposals have been made in the past for fiber-optic sensor devices which detect changes in the refractive index of a surrounding medium, for various applications. A conventional optical fiber has a light transmitting, optical fiber core of glass, an outer cladding of different refractive index from the core to prevent optical loss from the core, and an outer protective layer, usually of plastic. In U.S. Pat. Nos. 4,851,817 and 5,005,005 of Brossia et al., an optical fiber has portions of both the outer protective layer and the cladding layer removed, exposing the core. The exposed core is provided with striations by abrading or sanding it with a piece of sandpaper or the like. The sensor surface irregularities cause light to refract out of the fiber and into the surrounding medium, with the amount of light lost being dependent on the refractive index of the surrounding medium. A photodetector senses the amount of light transmitted along the fiber past the sensor portion. Changes in the amount of light transmitted provide an indication of changes in the surrounding medium. Brossia describes possible uses for this sensor device in providing an indication of icing conditions on aircraft, and also for soil moisture detection, detection of leakage from underground storage tanks, and for fluid level detection.

One problem with this sensor device is that the optical loss through a length of bare fiber core is very high. In fact, 90% or more of the light may be lost under such conditions. Thus, this device is only capable of detecting gross changes in the refractive index of a surrounding medium. This sensor device will not be sensitive enough to detect small changes in air humidity, for example.

SUMMARY OF THE INVENTION

It is an object of the present invention to provide a new and improved fiber-optic sensor device.

According to the present invention, a sensor device is provided which comprises an optical fiber having a core, a cladding layer surrounding the core, and an outer protective layer, at least a portion of the outer protective layer being removed to expose a portion of the cladding layer, and the exposed portion of the cladding layer being roughened to provide scratches which extend through at least part of the thickness of the cladding layer. One end of the fiber is connected to a suitable light source, while the opposite end is connected to a detector for detecting the amount of light transmitted through the fiber and producing an output signal proportional to the amount of light transmitted.

The roughened, exposed portion of the cladding layer is placed in a medium to be monitored. The light propagating through the fiber will suffer heightened scattering loss at its surface in the sensor region where the cladding is roughened and exposed. The amount of light lost will depend very strongly on the refractive index of the medium into which the fiber is immersed. In dry air, the scattering loss will be the highest, while high humidity air, which has a larger refractive index than dry air, will produce decreased scattering loss and more light transmitted through the fiber. Thus, the transmission loss is directly dependent on the humidity of the surrounding air, and an accurate measurement of humidity can be made.

The advantage of this technique over optical fiber sensors where the entire cladding layer is removed and the fiber surface is roughened is that less light will be lost, and thus a larger, more accurate signal is produced. The unaffected part of the cladding around the scratches will still act to retain light in the core, so that light can only escape through the roughened regions. This produces a much more accurate and sensitive device.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
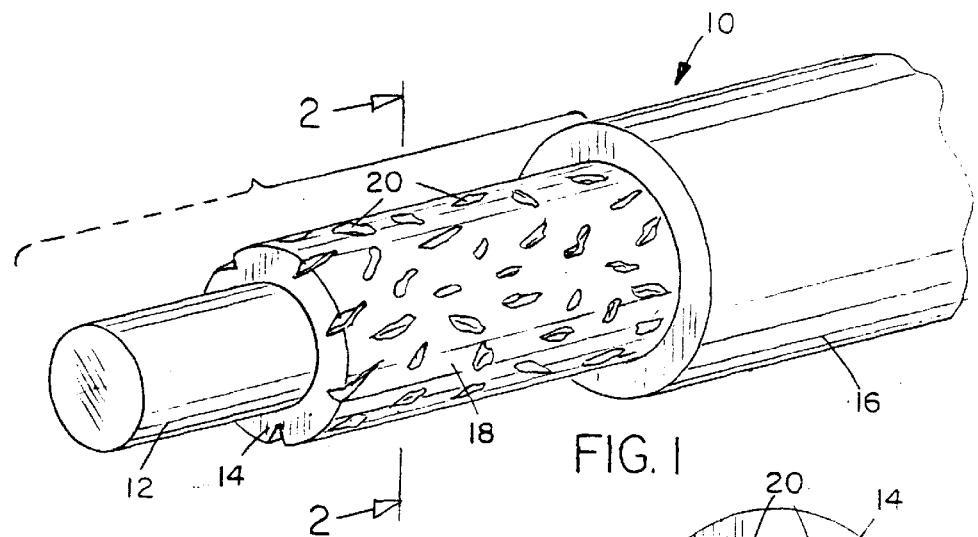
FIG. 1 is a perspective view of part of an optical fiber sensor element according to a preferred embodiment of the invention, with a portion of the cladding layer cut away to illustrate the surface roughening more clearly.
Figure 2:
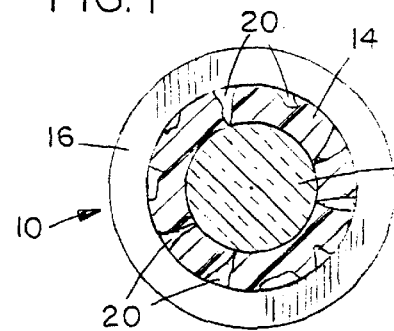
FIG. 2 is a sectional view taken on line 2—2 of FIG. 1.
Figure 3:
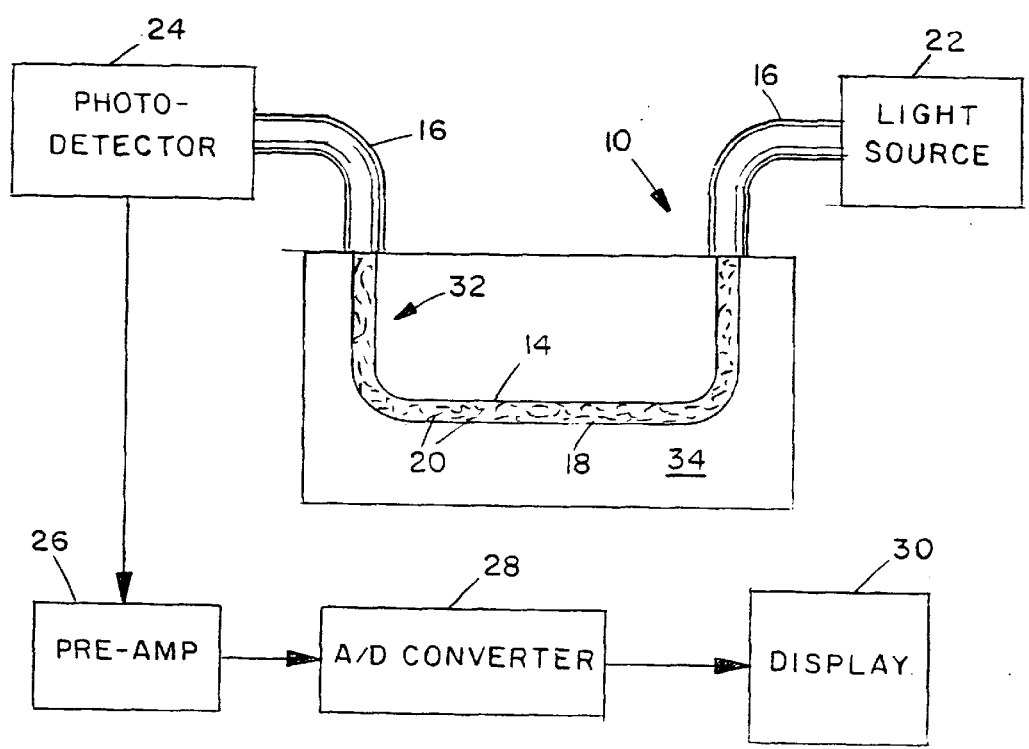
FIG. 3 illustrates one example of a sensor system incorporating the optical fiber sensor element.

FIGS. 1 and 2 of the drawings illustrate a fiber-optic sensor device 10 according to a preferred embodiment of the present invention, while FIG. 3 illustrates a possible sensor system for sensing changes in the refractive index of a surrounding medium utilizing the sensor device of FIGS. 1 and 2.

The sensor device 10 is made using a conventional optical fiber having a light transmitting fiber core 12 of fused silica or the like, a cladding layer 14 for preventing or restricting transmission of light radially out of the core, and a protective outer or buffer layer 16, which is usually of plastic material. It will be understood that this invention may be applied to any type of optical fiber and is not limited to fused silica glass fibers. The sensor element 10 has at least a portion of the outer buffer layer 16 stripped from the cladding layer and core, so that the outer surface 18 of the cladding layer is exposed along the length of the stripped portion. The outer layer 16 may be stripped using a standard optical fiber stripper, such as Model F-STR-125 of Newport Corp, or using a razor blade or the like. Although only a portion of the outer buffer layer is removed in the embodiment of FIGS. 1, 2 and 3, in some cases the buffer layer 16 may be removed along the entire length of the fiber. The length of the exposed portion 32 of the cladding layer is determined based on the desired sensitivity of the sensor, as discussed in more detail below.

The exposed surface 18 of the cladding layer is roughened by grinding with a selected grinding powder to produce a plurality of scratches or striations 20, with the number of scratches being dependent on the duration of the grinding process, and the depth of penetration of the scratches being dependent on the grinding powder used and the amount of force exerted on the grinding powder. It is important that the scratches do not extend into the fiber core, so the force exerted is such that each scratch extends partially or completely through the cladding layer but does not roughen the core. In a preferred embodiment of the present invention, a thick optical fiber is used. In such a fiber the cladding layer is of plastic and the core is of harder, glass material it will be relatively easy to ensure that no surface scratching of the glass core occurs, even where the scratches extend through the entire thickness of the cladding layer. The grinding powder selected will therefore be dependent on the thickness of the cladding layer. If the particle size of the grinding powder is greater than or equal to the cladding layer thickness, the majority of the scratches will extend through the entire thickness of the cladding layer. However, it is not essential that the scratches extend through the entire cladding layer, and light will still be lost via scratches that terminate short of the inner surface of the cladding layer.

In a preferred embodiment of the invention, where the cladding layer thickness was around 35 microns, a #40 grinding powder was used (abrasive size about 40 micron), although other grades of grinding powder may be used, depending on the desired surface roughness.

As illustrated in FIG. 3, one end of the sensor element or fiber 10 is connected to a suitable light source 22, which may be a laser diode, light emitting diode or other type of light source with coupling optics such as a microscope objective lens for transmitting light into the fiber. The opposite end is connected to a photodetector 24 such as a photodiode for detecting the light transmitted through the fiber 10 and producing an output signal proportional to the transmitted light intensity $I_1$. The output signal from the photodetector is connected via pre-amplifier 26 and analog to digital (A/D) converter 28 to a suitable output display and/or printer unit 30.

The exposed, roughened cladding layer defines a sensor portion 32 of the sensor element which is exposed to a medium 34 to be monitored, which may be a liquid or a gas, such as air, for example. The light propagating through the fiber core 12 will suffer an increased scattering loss along the sensor portion 32. The scattering loss has been found to be highly dependent on the refractive index of the surrounding medium. Thus, changes in the refractive index due to changing conditions can be monitored with the system of FIG. 3. For example, if the medium 34 is air, the system may be used to monitor humidity. Dry air has a lower refractive index than humid air. Thus, the scattering loss will be higher in dry air than in humid air. As scattering loss decreases, more light is transmitted through the fiber. The amount of light transmitted through the fiber will therefore be dependent on the refractive index, and thus the humidity, of the surrounding air. The output signal from photodetector 24 can be suitably processed to produce an output corresponding to the physical quantity to be monitored, such as relative humidity or refractive index.

The following equation has been derived to calculate the transmission loss from the surface roughened cladding layer. If $\alpha_s$ is the surface scattering loss, then $$\alpha_s = \frac{2Nr^2}{(\pi R^2)} \left\{ \frac{(1+m)^{0.5}}{2^{0.5}} - m + \frac{2m(1-m)^2}{(1+m)^2} \right\} \quad (1)$$

$$m = \frac{n_2}{n_1}$$

where r is the surface roughness of the exposed portion of the cladding layer measured as the depth of surface scratch, R is the diameter of the fiber core, N is the number density (per unit length) of the surface scratches, $n_1$ is the refractive index of the fiber cladding layer, and $n_2$ is the refractive index of the surrounding medium. If the length of the surface roughened portion of the cladding layer is l, and the incident light intensity is $I_0$, then the transmitted light intensity through the fiber will be:

$$I_t = I_0 e^{-\alpha_s l} \quad (2)$$

By using equation (1), an optical fiber can be designed with the desired sensitivity and measurement range, depending on the preferred application and likely variation in the property to be measured. A suitably programmed microprocessor may be used to convert the output signal of the photodetector to the desired quantity, such as refractive index, using equations (1) and (2) above, as will be understood by those skilled in the field.

In one example, the cladding layer had an index of refraction $n_1$ of 1.457, the surrounding medium was dry air having an index of refraction $n_2$ of around 1, the depth of a scratch was 5 micron (r), radius of the fiber core was 1 mm and the number density N of scratches was 2000 per cm. For this particular example, the surface scattering loss coefficient $\alpha_s$ is 0.009 cm, the length of the roughened fiber sensor portion is 10 cm, the total scattering loss through the sensor portion of the fiber can be calculated as follows:

$$1 - e^{-\alpha_s l} = 1 - \exp(0.009 \times 10)$$
$$= 1 - 0.91$$
$$= 9.$$

Conversely, if the scattering loss is known, based on the input light intensity and the received light intensity, the refractive index of the surrounding medium can be calculated accurately.

The sensitivity of the sensor device of this invention will be greater than that of other known fiber-optic sensors where the cladding layer is completely removed and the core itself has its surface roughened. This is because the amount of light lost in this invention is significantly reduced, and the output light intensity will therefore be higher, and more sensitive to smaller variations in the refractive index of the surrounding medium. If the entire cladding layer is removed along a length of around 2 cm of the fiber, the optical loss through the length of bare fiber core is such that more than 90% of the light is lost, in other words only 10% of the incident light is transmitted to the end of the fiber. Such a heavy loss prevents any sensitive measurement of variations in the refractive index of the surrounding medium. The change in the refractive index must be gross in order to be detectable with such a sensor.

In contrast, in the present invention, a much smaller percentage of the incident light will be lost in the sensor portion. The amount of light lost will be dependent on the length of the sensor portion, and the number and depth of the scratches in the cladding layer, in addition to the refractive index of the surrounding region. In a typical example where a sensor portion had a length of 10 cm, the amount of light lost was of the order of 9%. This is because the majority of the cladding layer remains in place along the sensor portion, and the portions of the cladding layer between the scratches 20 will retain light inside the fiber core. Light can escape only through the roughened portions or scratches 20, enhancing the sensitivity of the device.

In one specific example of the invention, the optical fiber had a core diameter of 1 mm and a plastic cladding layer diameter of 1.035 mm. The length of the sensor portion over which the outer protective layer is removed may be between 2 cm to the entire length of the fiber, depending on the quantity to be measured and the type of medium in which the sensor portion is to be immersed.

The sensor element 10 is capable of detecting a very small change in the refractive index of a medium into which the sensor portion 32 is immersed, and can be used in liquid, gaseous, or granular solid media. In addition to detecting humidity changes in air, it may also be used in other applications. The sensor fiber is of glass, and is therefore chemically inert and mechanically rugged, so the device can be used in hostile, volatile and corrosive environments without breakdown. There are numerous other possible applications, such as car battery monitoring, liquid refractometer, cement drying monitor, agricultural product humidity monitor, baking monitor, soil water and contaminant detection, water and icing detector, exhaust gas monitoring, and sugar content monitoring.

In order to monitor a car battery's chemical composition as the battery ages, the sensor fiber of this invention may be immersed in the battery liquid. This provides an indication of the condition of the battery.

The sensor fiber may also be used as a liquid refractometer to provide a convenient and accurate measurement of the index of refraction of a liquid, chemical solution, or solvent into which the sensor portion of the fiber is immersed.

In a construction site, the poured cement needs to be monitored to determine whether it is sufficiently dried before additional work can be built upon it. The fiber sensor of this invention can serve as a disposable probe to be buried in wet cement and monitor its drying.

The fiber sensor may also be inserted into a pile of grain or other agricultural products to detect humidity inside the pile. Another possible application is in monitoring humidity inside a baking oven, such as a bread baking oven or an oven used in tobacco processing. The fiber sensor is sufficiently rugged to be used in such an application.

The fiber sensor may also be submerged into soil to detect water and contaminants. It may also be used to monitor exhaust gas in a car exhaust pipe, for example. Exhaust gases resulting from incomplete combustion will contain more pollutants will have a different refractive index from exhaust gases resulting from efficient combustion, and the sensor device can therefore differentiate between these different types of exhaust gases. The sensor may also be used to monitor sugar content in a solution, since the refractive index of the solution will vary with changes in sugar content.

There are many other possible applications for the sensor device and system of this invention. The sensor device may be used to monitor any medium to detect changes in refractive index which may result from change in humidity or water level, change in pollutant levels, changes in chemical composition, and the like. The sensor device of this invention is relatively inexpensive, yet provides a sensitive measurement of any change in refractive index of a surrounding medium, and thus of the property which caused that change. Although other possible applications are discussed above, this device is particularly useful as a humidity sensor, where the change in refractive index may be relatively small. Other known humidity sensors are expensive to manufacture and slow to respond to humidity changes. The sensor device of this invention, if used as a humidity sensor, is relatively inexpensive yet very accurate, even in detecting relatively small changes in humidity.

Although a preferred embodiment of the present invention is described above by way of example only, it will be understood by those skilled in the field that modifications may be made to the disclosed embodiment without departing from the scope of the present invention, which is defined by the appended claims.

We claim:

1. A sensor device, comprising:
    a length of optical fiber having a core, a cladding layer surrounding the core, and an outer protective layer;
    at least a portion of the length of the optical fiber having the outer protective layer removed to expose a portion of the cladding layer;
    the exposed portion of the cladding layer being roughened, whereby a part of the light propagating through the core will be lost through the exposed, roughened portion of the cladding, the amount of light lost being dependent on the refractive index of a medium surrounding the exposed portion of the cladding layer; and
    the exposed portion of the cladding layer extending along a part of the length of the optical fiber, and the outer protective layer covering the cladding layer on each side of the exposed portion.

2. The device as claimed in claim 1, wherein the exposed portion has a length of at least 1 cm.

3. The device as claimed in claim 1, wherein the cladding layer has a thickness of about 35 micron and the surface of the cladding layer is roughened with a grinding powder having an abrasive size of about 40 micron.

4. The device as claimed in claim 1, wherein the cladding layer is of predetermined thickness, and the roughened portion has scratches of depth no greater than the thickness of the cladding layer.

5. The device as claimed in claim 4, wherein at least some of the scratches are of depth equal to the depth of the cladding layer, whereby portions of the outer surface of the core are exposed, the exposed portions being smooth and non-roughened.

6. A sensor system, comprising:
    a light source;
    an optical fiber having a first end positioned to receive output light from the light source, and a second end;
    the optical fiber having a light transmitting core, a cladding layer surrounding the core, and an outer protective layer, the outer protective layer being removed along at least part of the length of the fiber to expose a portion of the cladding layer;
    the exposed portion of the cladding layer being roughened to produce a plurality of surface scratches extending through at least part of the thickness of the cladding layer, whereby the exposed, roughened portion of the cladding layer forms a sensor region through which light is lost from the core; and
    a photodetector connected to the second end of the optical fiber for detecting the amount of light transmitted through the fiber and producing an output signal proportional to the amount of light transmitted;

whereby the sensor is immersed in a medium to be monitored and the amount of light lost through the sensor is dependent on the refractive index of the medium.

7. The system as claimed in claim 6, wherein the surface of the exposed cladding portion is roughened with a grinding powder having an abrasive size in the range from 30 micron to 50 micron.

8. The system as claimed in claim 7, wherein the cladding layer has a thickness of about 35 micron and the cladding portion is roughened with a grinding powder having an abrasive size of about 40 micron, and the core has a smooth, unabraded surface.

9. The system as claimed in claim 6, wherein the scratches have a depth no greater than the thickness of the cladding layer and the core has a surface which is smooth and not roughened in the sensor region.

10. The system as claimed in claim 6, wherein the sensor region extends along part of the length of the optical fiber in an intermediate portion of the optical fiber terminating short of the opposite ends of the fiber.

11. A humidity sensor system, comprising:

a light source having an output light beam;

an optical fiber having a first end positioned to receive the output light beam from the light source, and a second end;

the fiber having a light transmitting core and a cladding layer surrounding the core;

the cladding layer having a surface roughened portion extending along at least part of the length of the fiber;

the surface roughened portion comprising means for exposing to a medium of variable humidity to detect humidity changes, whereby a portion of the light transmitted through the core will be lost through the surface roughened portion of the cladding layer and the amount of light transmitted through the core to the second end will be dependent on the refractive index of the surrounding medium;

a photodetector connected to the second end of the fiber for detecting the amount of light transmitted and producing an output signal proportional to the received light intensity; and signal processing means connected to the photodetector for receiving the output signal and processing the signal to produce an output corresponding to the refractive index of the surrounding medium.

12. The system as claimed in claim 11, wherein the surface roughened portion has a plurality of scratches extending through at least part of the thickness of the cladding layer, and the core has a smooth, unabraded surface underlying the surface roughened portion of the cladding layer.

13. A method of making a fiber-optic sensor element, comprising the steps of:

taking a length of optical fiber having a core, a cladding layer surrounding the core, and an outer protective layer;

stripping at least a portion of the outer protective layer from the fiber to expose at least a portion of the length of the cladding layer;

roughening the surface of the exposed portion of the cladding layer to produce a plurality of scratches extending at least partially through the thickness of the cladding layer but leaving the core smooth and unabraded; and connecting a first end of the fiber to al light source and the second end to a detector for detecting the amount of light transmitted through the fiber, whereby the amount of light lost through the roughened portion of the cladding layer will be dependent on the refractive index of a surrounding medium.

14. A method of detecting the refractive index of a medium, comprising the steps of:

placing a sensor portion of an optical fiber in a medium to be monitored, the sensor portion having a roughened cladding layer exposed to the medium;

transmitting light along the core of the optical fiber from a first end to a second end of the fiber, whereby a portion of the transmitted light will be lost through the roughened cladding layer in the sensor portion, the amount of light lost being dependent on the refractive index of the medium;

detecting the intensity of light received at the second end of the fiber; and using the detected light intensity to determine the refractive index of the medium.

* * * * *

UNITED STATES PATENT AND TRADEMARK OFFICE
CERTIFICATE OF CORRECTION

PATENT NO. : 5,995,686
DATED : November 30, 1999
INVENTOR(S) : Robert N. Hamburger, *et al.*

It is certified that error appears in the above-identified patent and that said Letters Patent is hereby corrected as shown below:

On the title page, item [76]

In Inventors, line 6, please delete "Tuscon" and substitute --Tucson-- therefor.

In column 4, line 40, please delete " = 9." and substitute -- = 9 %. -- therefor.

Signed and Sealed this

Twenty-seventh Day of June, 2000

Attest:

Q. TODD DICKINSON

*Attesting Officer*  *Director of Patents and Trademarks*